(12) United States Patent
Collazo et al.

(10) Patent No.: US 9,526,513 B2
(45) Date of Patent: Dec. 27, 2016

(54) VOID FILLING JOINT PROSTHESIS AND ASSOCIATED INSTRUMENTS

(71) Applicant: Howmedica Osteonics Corp., Mahwah, NJ (US)

(72) Inventors: Carlos E. Collazo, Old Greenwich, CT (US); Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 268 days.

(21) Appl. No.: 14/206,630

(22) Filed: Mar. 12, 2014

(65) Prior Publication Data

US 2014/0276882 A1    Sep. 18, 2014

Related U.S. Application Data

(60) Provisional application No. 61/779,302, filed on Mar. 13, 2013.

(51) Int. Cl.
*A61B 17/17*  (2006.01)
*A61B 17/16*  (2006.01)
*A61F 2/30*  (2006.01)
*A61F 2/38*  (2006.01)

(52) U.S. Cl.
CPC ............ *A61B 17/17* (2013.01); *A61B 17/164* (2013.01); *A61B 17/1675* (2013.01); *A61B 17/1764* (2013.01); *A61F 2/30724* (2013.01); *A61F 2/30734* (2013.01); *A61B 2090/062* (2016.02); *A61F 2/3859* (2013.01); *A61F 2002/30736* (2013.01)

(58) Field of Classification Search
CPC ............................. A61F 17/17; A61F 17/1764
See application file for complete search history.

(56) References Cited

U.S. PATENT DOCUMENTS

| 3,924,274 A | 12/1975 | Heimke et al. |
| 3,986,212 A | 10/1976 | Sauer |
| 4,065,817 A | 1/1978 | Branemark et al. |
| 4,306,550 A | 12/1981 | Forte |
| 4,341,206 A | 7/1982 | Perrett et al. |

(Continued)

FOREIGN PATENT DOCUMENTS

| DE | 2842847 A1 | 4/1980 |
| EP | 0016480 A1 | 10/1980 |

(Continued)

OTHER PUBLICATIONS

Schreurs, et al., Femoral Component Revision with Use of Impaction Bone-Grafting and a Cemented Polished Stem. Surgical Technique, The Journal of Bone & Joint Surgery, 2006, pp. 259-274.

(Continued)

*Primary Examiner* — Andrew Yang
(74) *Attorney, Agent, or Firm* — Lerner, David, Littenberg, Krumholz & Mentlik, LLP

(57) ABSTRACT

A bone void filling prosthesis, which includes a body and a plurality of legs. The body includes an aperture extending therethrough. The plurality of legs are each connected to the body. Each of the plurality of legs includes at least one selectively removable portion for adjusting a length of each of the plurality of legs.

24 Claims, 19 Drawing Sheets

(56) References Cited

U.S. PATENT DOCUMENTS

| | | | |
|---|---|---|---|
| 4,463,444 | A | 7/1984 | Daniels et al. |
| 4,549,319 | A | 10/1985 | Meyer |
| 4,681,589 | A | 7/1987 | Tronzo |
| 4,693,721 | A | 9/1987 | Ducheyne |
| 4,728,335 | A | 3/1988 | Jurgutis |
| 4,735,625 | A | 4/1988 | Davidson |
| 4,738,256 | A | 4/1988 | Freeman et al. |
| 4,751,922 | A | 6/1988 | DiPietropolo |
| 4,777,942 | A | 10/1988 | Frey et al. |
| 4,790,852 | A | 12/1988 | Noiles |
| 4,822,366 | A | 4/1989 | Bolesky |
| 4,846,839 | A | 7/1989 | Noiles |
| 5,011,496 | A | 4/1991 | Forte et al. |
| 5,035,717 | A | 7/1991 | Brooks |
| 5,047,033 | A | 9/1991 | Fallin |
| 5,049,157 | A | 9/1991 | Mittelmeier et al. |
| 5,061,287 | A | 10/1991 | Feiler |
| 5,122,134 | A | 6/1992 | Borzone et al. |
| 5,152,797 | A | 10/1992 | Luckman et al. |
| 5,190,548 | A | 3/1993 | Davis |
| 5,192,283 | A | 3/1993 | Ling et al. |
| 5,342,363 | A | 8/1994 | Richelsoph |
| 5,342,366 | A | 8/1994 | Whiteside et al. |
| 5,387,218 | A | 2/1995 | Meswania |
| 5,403,320 | A | 4/1995 | Luman et al. |
| 5,411,505 | A * | 5/1995 | Mumme ............ A61B 17/155 606/88 |
| 5,445,642 | A | 8/1995 | McNulty et al. |
| 5,480,453 | A | 1/1996 | Burke |
| 5,489,311 | A | 2/1996 | Cipolletti |
| 5,496,324 | A | 3/1996 | Barnes |
| 5,527,316 | A | 6/1996 | Stone et al. |
| 5,534,005 | A | 7/1996 | Tokish, Jr. et al. |
| 5,540,694 | A | 7/1996 | DeCarlo, Jr. et al. |
| 5,591,233 | A | 1/1997 | Kelman et al. |
| 5,634,927 | A * | 6/1997 | Houston ............ A61B 17/1735 606/79 |
| 5,649,299 | A | 7/1997 | Battin et al. |
| 5,755,720 | A | 5/1998 | Mikhail |
| 5,755,793 | A | 5/1998 | Smith et al. |
| 5,782,921 | A | 7/1998 | Colleran et al. |
| 5,824,097 | A | 10/1998 | Gabriel et al. |
| 5,931,841 | A | 8/1999 | Ralph |
| 5,951,603 | A | 9/1999 | O'Neil et al. |
| 5,957,925 | A | 9/1999 | Cook et al. |
| 5,976,145 | A | 11/1999 | Kennefick, III |
| 5,976,147 | A | 11/1999 | LaSalle et al. |
| 5,984,968 | A | 11/1999 | Park |
| 5,989,257 | A | 11/1999 | Tidwell et al. |
| 5,993,455 | A | 11/1999 | Noble |
| 6,010,534 | A | 1/2000 | O'Neil et al. |
| 6,053,945 | A | 4/2000 | O'Neil et al. |
| 6,071,311 | A | 6/2000 | O'Neil et al. |
| 6,139,584 | A | 10/2000 | Ochoa et al. |
| 6,152,963 | A | 11/2000 | Noiles et al. |
| 6,171,342 | B1 | 1/2001 | O'Neil et al. |
| 6,214,052 | B1 | 4/2001 | Burkinshaw |
| 6,214,053 | B1 | 4/2001 | Ling et al. |
| 6,241,722 | B1 | 6/2001 | Dobak et al. |
| 6,245,113 | B1 | 6/2001 | Revie et al. |
| 6,440,171 | B1 | 8/2002 | Doubler et al. |
| 6,494,913 | B1 | 12/2002 | Huebner |
| 6,702,822 | B1 | 3/2004 | Noiles et al. |
| 6,887,276 | B2 | 5/2005 | Gerbec et al. |
| 6,945,556 | B2 | 9/2005 | Maertens |
| 7,074,224 | B2 | 7/2006 | Daniels et al. |
| 7,090,677 | B2 | 8/2006 | Fallin et al. |
| 7,255,702 | B2 | 8/2007 | Serra et al. |
| 7,291,174 | B2 | 11/2007 | German et al. |
| 7,297,163 | B2 | 11/2007 | Huebner |
| 7,393,355 | B2 | 7/2008 | Tulkis et al. |
| 7,481,814 | B1 | 1/2009 | Metzger |
| 7,537,664 | B2 | 5/2009 | O'Neill et al. |
| 7,785,328 | B2 | 8/2010 | Christie et al. |
| 7,799,085 | B2 | 9/2010 | Goodfried et al. |
| 7,892,288 | B2 | 2/2011 | Blaylock et al. |
| 7,892,290 | B2 | 2/2011 | Bergin et al. |
| 7,918,892 | B2 | 4/2011 | Huebner |
| 7,942,879 | B2 | 5/2011 | Christie et al. |
| 8,029,573 | B2 | 10/2011 | Podolsky |
| 8,147,861 | B2 | 4/2012 | Jones et al. |
| 8,167,882 | B2 | 5/2012 | Sackett et al. |
| 8,177,788 | B2 | 5/2012 | McLean et al. |
| 8,187,336 | B2 | 5/2012 | Jamali |
| 8,350,186 | B2 | 1/2013 | Jones et al. |
| 8,372,157 | B2 | 2/2013 | Petersen et al. |
| 8,382,849 | B2 | 2/2013 | Thomas |
| 8,424,183 | B2 | 4/2013 | Thomas |
| 8,444,699 | B2 | 5/2013 | Metzger et al. |
| 8,506,645 | B2 | 8/2013 | Blaylock et al. |
| 8,585,770 | B2 | 11/2013 | Meridew et al. |
| 8,900,317 | B2 | 12/2014 | Zubok et al. |
| 9,011,444 | B2 | 4/2015 | Primiano et al. |
| 2003/0171756 | A1 | 9/2003 | Fallin et al. |
| 2004/0049285 | A1 | 3/2004 | Haas |
| 2004/0162619 | A1 | 8/2004 | Blaylock et al. |
| 2005/0288676 | A1 | 12/2005 | Schnieders et al. |
| 2006/0147332 | A1 | 7/2006 | Jones et al. |
| 2007/0088443 | A1 | 4/2007 | Hanssen et al. |
| 2007/0118229 | A1 | 5/2007 | Bergin et al. |
| 2007/0142914 | A1 | 6/2007 | Jones et al. |
| 2007/0162033 | A1 | 7/2007 | Daniels et al. |
| 2009/0157190 | A1 | 6/2009 | Collazo et al. |
| 2010/0076565 | A1 | 3/2010 | Thomas |
| 2010/0082031 | A1 | 4/2010 | Sackett et al. |
| 2010/0114323 | A1 | 5/2010 | Deruntz et al. |
| 2010/0222891 | A1 | 9/2010 | Goodfried et al. |
| 2011/0190899 | A1 | 8/2011 | Pierce et al. |
| 2012/0016482 | A1 | 1/2012 | Mooradian et al. |
| 2012/0089146 | A1 | 4/2012 | Ferko et al. |
| 2012/0226281 | A1 | 9/2012 | Sackett et al. |
| 2013/0053976 | A1 | 2/2013 | Gugler et al. |
| 2013/0172892 | A1 | 7/2013 | Servidio et al. |
| 2013/0211536 | A1 | 8/2013 | Metzger et al. |
| 2013/0264749 | A1 | 10/2013 | Jones et al. |

FOREIGN PATENT DOCUMENTS

| | | |
|---|---|---|
| EP | 2168586 A1 | 3/2010 |
| EP | 2181672 A1 | 5/2010 |
| GB | 2159416 A | 12/1985 |
| WO | 03094698 A2 | 11/2003 |
| WO | 2006127486 A2 | 11/2006 |
| WO | 2008069800 A1 | 6/2008 |

OTHER PUBLICATIONS

Lonner, et al., Impaction Grafting and Wire Mesh for Uncontained Defects in Revision Knee Arthroplasty, Clinical Orthopaedics and Related Research, No. 404, pp. 145-151, Copyright 2002, Lippincott Williams & Wilkins, Inc.

Stryker Howmedica Osteonics, X-change Revision Instruments System, Copyright Howmedica Osteonics 2001.

Knee Revision Product Portfolio, DePuy International Ltd., a Johnson & Johnson Company, Cat. No. 9075-40-000 version 1, Copyright 2009.

Zimmer, Trabecular Metal, Tibial and Femoral Cones Surgical Techniques, Copyright 2011.

International Search Report and Written Opinion for Application No. PCT/US2012/068473 dated Mar. 8, 2013.

International Search Report and Written Opinion for Application No. PCT/US2012/072087 dated May 2, 2013.

Partial International Search Report dated Mar. 15, 2013 for Application No. PCT/US2012/072087.

U.S. Appl. No. 13/441,154, filed Apr. 6, 2012.

Extended European Search Report for Application No. EP14159399 dated Jun. 6, 2014.

* cited by examiner

VOID FILLING JOINT PROSTHESIS AND ASSOCIATED INSTRUMENTS

CROSS-REFERENCE TO RELATED APPLICATIONS

The present application claims the benefit of the filing date of U.S. Provisional Patent Application No. 61/779,302 filed Mar. 13, 2013, the disclosure of which is hereby incorporated herein by reference.

BACKGROUND OF THE INVENTION

Joint replacement surgery is a common orthopedic procedure for joints such as the shoulder, hip, knee, ankle and wrist. Prior to implanting prosthetic components in a joint of a patient, a surgeon generally has to resect at least a portion of the patient's native bone in order to create a recess or void for receiving at least a portion of the prosthetic components being implanted. During the process of resecting bone, a surgeon generally only resects the amount of bone that is needed in order to properly implant the prosthetic components in the joint. Once native bone is resected from a joint, it is gone forever. Thus, the surgeon typically attempts to maintain as much native structural integrity of the joint as he or she can during the resection process.

When previously implanted prosthetic components fail for any one of a variety of reasons, a revision procedure is often necessary. An issue generally encountered by surgeons replacing joints during a revision procedure is the additional loss of native bone near the joint being replaced. This bone loss is typically due to movement of the component or components after implantation or even degeneration or further degeneration of the bone, which can form bone voids that have unpredictable and non-uniform shapes.

When bone voids are observed in either the proximal tibia or distal femur, or both, it is standard surgical practice to fill those voids as part of the revision surgical procedure. The preferred practice is to fill those voids with weight bearing void fillers, typically made of an implant-grade metal such as titanium. However, because the bone voids are typically irregular in shape, some preparation of the bone void area is typically required prior to implantation of the void filler. This preparation (typically by reaming, broaching or milling) ensures there is sufficient room in the bone void for the void filler. An accurate fit between the shaped bone void and the void filler is also important for establishing joint line, and allowing for weight bearing and bone remodeling during the recovery process.

Different methods are commonly used to attempt to prepare the bone void area to create an accurate fit between the shaped bone void and void filler. One method is to ream along the intramedullary ("IM") axis, followed by broaching. Another method is to ream along the IM axis, followed by freehand burring or rongeur bone removal, which may also be followed by broaching. Problems with these methods include that reaming is performed on the IM axis only, so that void areas at a distance from the IM axis, which commonly occur, can only be resected using manual methods. Moreover, broaching generally has at least two problems. First, a manual operation can be time consuming, particularly in cases of sclerotic bone, which exposes the patient to an increased risk of infection and longer recovery. Second, in the case of large bone voids, broaching generally needs to be performed in a multi-step process because attempting to remove high volumes of bone in a single broaching step generally requires high impact forces to the bone. Also, freehand bone removal, either powered or unpowered, such as with a burr or rongeur, often does not produce accurate void shapes to receive predefined prosthetic components. A typical result is that areas remain where the outer walls of the void filler do not contact the void, which may lead to undesirable stress distribution and possible loss of bone regrowth. Also typical is the time consuming requirement of iterative bone removal, with multiple checks against the void fillers, to obtain a correct fit.

Occasionally the bone loss or bone deformity is so significant that the surgeon must resect a portion of bone along its length and supplement the bone loss with a bone augment. Since the surgeon typically attempts to preserve as much native bone as possible, the result of the resection is typically a bone that has multilevel plateaus, where the bone augment is commonly placed between the joint prosthesis and one plateau in order to augment the missing bone, and the prosthesis itself is placed against the other plateau. However, this resection generally does not eliminate the need for a void filler. Generally, the bone void extends through the multilevel plateaus, which creates an area where the void filler would be exposed and would interfere with the placement of the bone augment when implanted. Unfortunately, this situation is often unpredictable as the surgeon is often unaware of the need to augment until the previous prosthesis has been removed.

Thus, there is a need for a bone void filler that is adaptable to be used in both a joint revision procedure requiring a bone augment so as to not interfere with the placement of the augment and a joint revision procedure where a bone augment is not needed.

BRIEF SUMMARY OF THE INVENTION

According to a first embodiment of the present invention, a bone void filling prosthesis is disclosed herein. The bone void filling prosthesis includes a body that includes an aperture extending therethrough, a plurality of legs each connected to the body. Each of the legs including at least one selectively removable portion for adjusting a length of each of the plurality of legs.

Further, the at least one selectively removable portion may include a first portion and a second portion. The first portion may be constructed from weaker material, while the second portion maybe constructed from stronger material. The first portion and second portion may be layered along the length of the at least one of the plurality of legs. Additionally the weaker material may be porous titanium including a first porosity. Further, the stronger material may be porous titanium including a second porosity. The first porosity may be greater than the second porosity. Additionally, the weaker material is visually distinct from the stronger material.

Continuing with the first embodiment, each leg may include a plurality of selectively removable portions layered along the length of each leg. Further, the body may be cylindrically shaped and the prosthesis may include two legs, and each of the two legs may include a plurality of selectively removable portions. Further, each of the two legs may be substantially frustoconically shaped and one end of each of the two legs may be partially integrated with the central body. Additionally, the two legs may be separated by a space forming a saddle for receipt of a femoral cam box of a femoral implant. The space may be in communication with the aperture of the central body. Also, one end of each of the two legs may further include a conical portion extending from the first end. The conical portion maybe partially integrated with the central body.

According to another embodiment of the present invention, a bone void filling prosthesis that includes a substantially cylindrical body having an aperture extending therethrough and an exterior surface disposed opposite the aperture. Also, included is a first substantially frustoconical leg having a first end and a second end. The first end being integrated with the exterior surface such that the first leg extends away from the central body. The second end having at least one first selectively removable portion for adjusting a length of the first leg. Further included in the bone filling prosthesis is a second substantially frustoconical leg. The second substantially frustoconical leg includes a first end and a second end. The first end of the second leg may be integrated with the exterior surface such that the second leg extends away from the central body. The second end of the first leg may include at least one second selectively removable portion for adjusting a length of the second leg.

Further, the first leg may include a plurality of first selectively removable portions layered along the length of the first leg, and the second leg may include a plurality of second selectively removable portions layered along the length of the second leg. Additionally, each of the plurality of first selectively removable portions may include a first portion and a second portion. The first portion may be constructed from weaker material, and the second portion may be constructed from stronger material. The first portion and second portion may be layered along the length of the first leg. Each of the plurality of second selectively removable portions may include a first segment and a second segment. The first segment may be constructed from weaker material, and the second segment may be constructed from stronger material. Also, the first segment and second segment may be layered along the length of the second leg.

Continuing with this embodiment, the weaker material may include porous titanium that may include a first porosity. Further, the stronger material may be porous titanium that may include a second porosity. The first porosity may be greater than the second porosity. Additionally, the weaker material may be visually distinct from the stronger material.

The two legs may be separated by a space forming a saddle for receipt of a femoral cam box of a femoral implant. The space may be in communication with the aperture of the body. Additionally, the first ends of each of the first leg and second leg may further include conical portions integrated with the body.

According to one embodiment of the present invention, a method of forming a bone void for receipt of a prosthesis. The method may include inserting a stem of a reaming guide assembly into an intramedullary canal of a bone. The reaming guide assembly may include first and second reamer guides disposed adjacent to each other. The first and second reamer guides may be connected to an end of the stem. Further included in the method is reaming the bone through the aperture of the first reamer guide to form a first bone void. The method also includes inserting the lobe trial into the first bone void. Additionally included in the method is reaming the bone through the aperture of the second reamer guide to form a second bone void.

Further, the first and second reamer guide may each include an aperture defining a sidewall and a slot extending along the length of the sidewall. The slot may be in communication with the aperture. Additionally, the method may include the step of loading a reamer through the slot of the first reamer guide into the aperture of the first reamer guide. Further, the method may include the step of loading a lobe trial through the slot of the first reamer guide into the aperture of the first reamer guide. Another step that may be included is the step of loading the reamer through the slot of the second reamer guide into the aperture of the second reamer guide

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1:
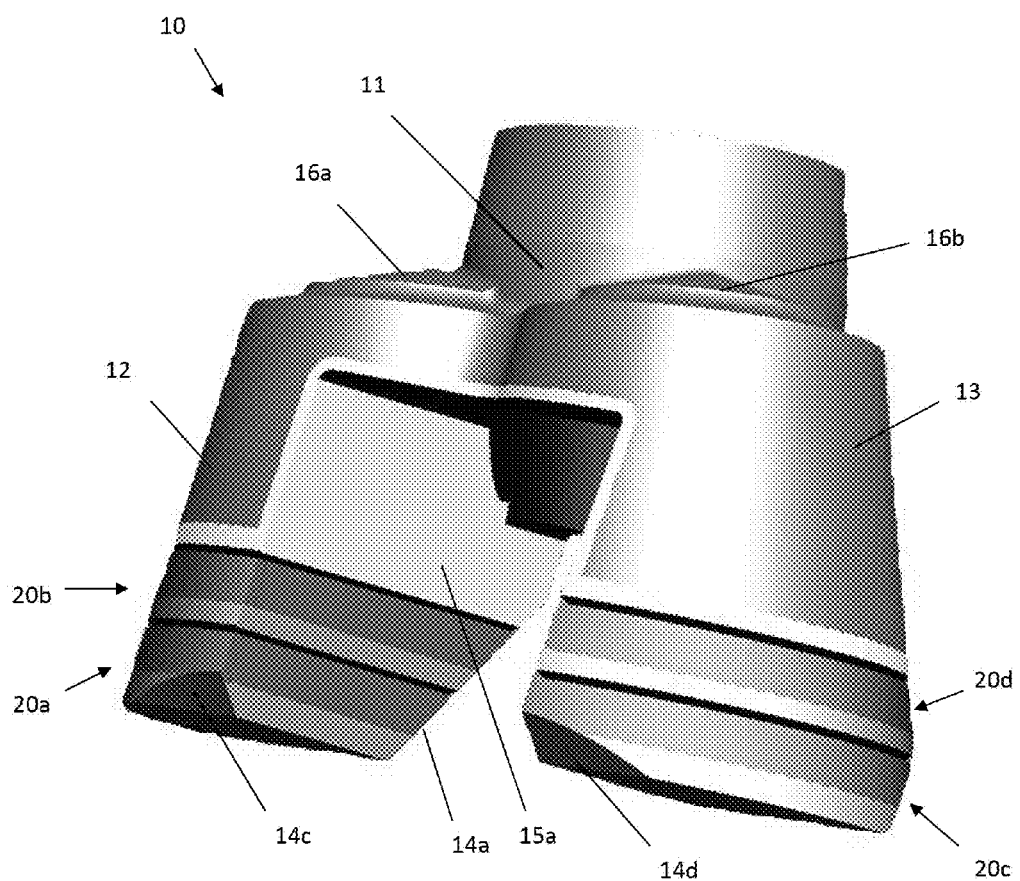
FIG. 1 shows a perspective view of one embodiment of a void filling prosthesis.
Figure 2:
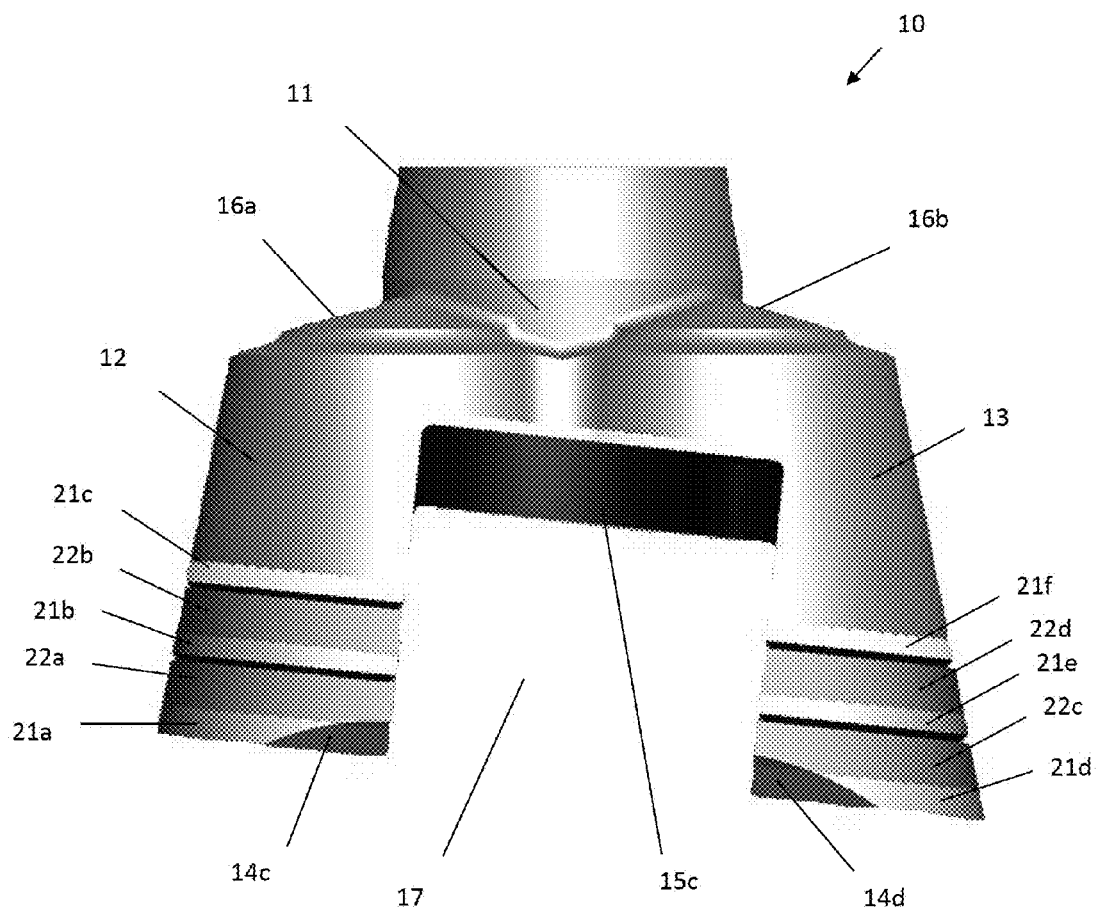
FIG. 2 shows a front view of the void filling prosthesis of FIG. 1.
Figure 3:
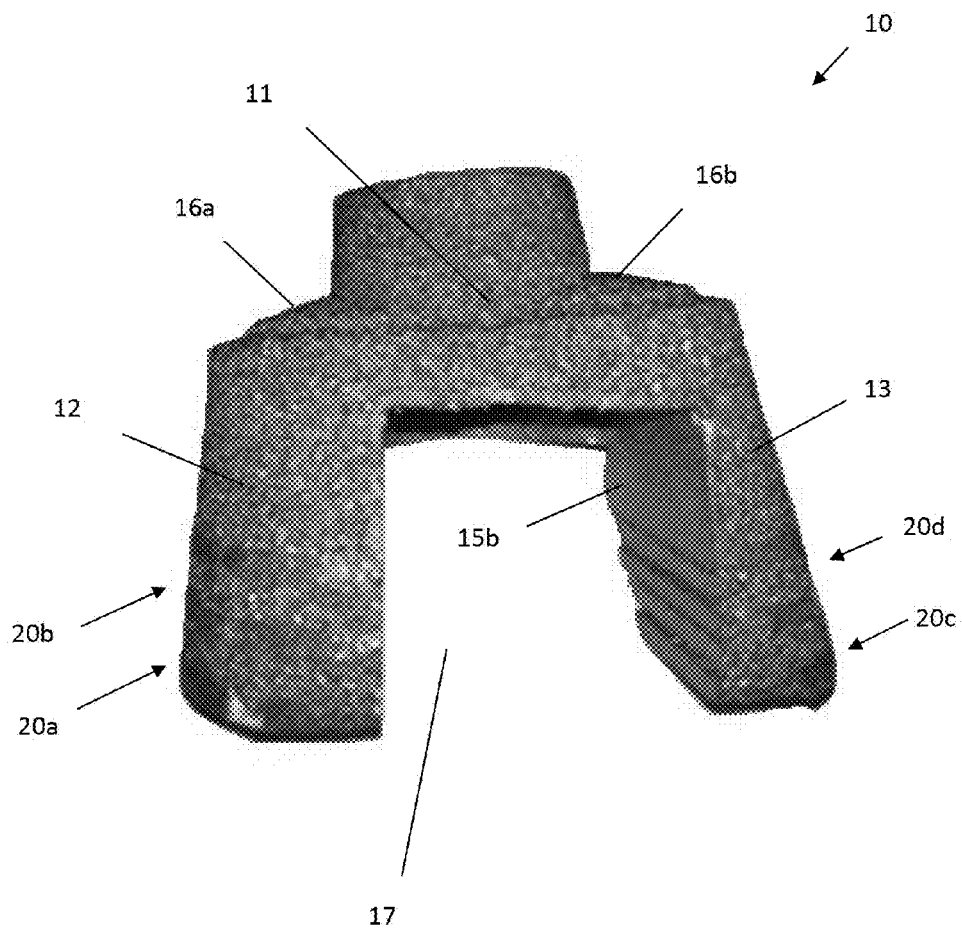
FIG. 3 shows another perspective view of the void filling prosthesis of FIG. 1.
Figure 4:
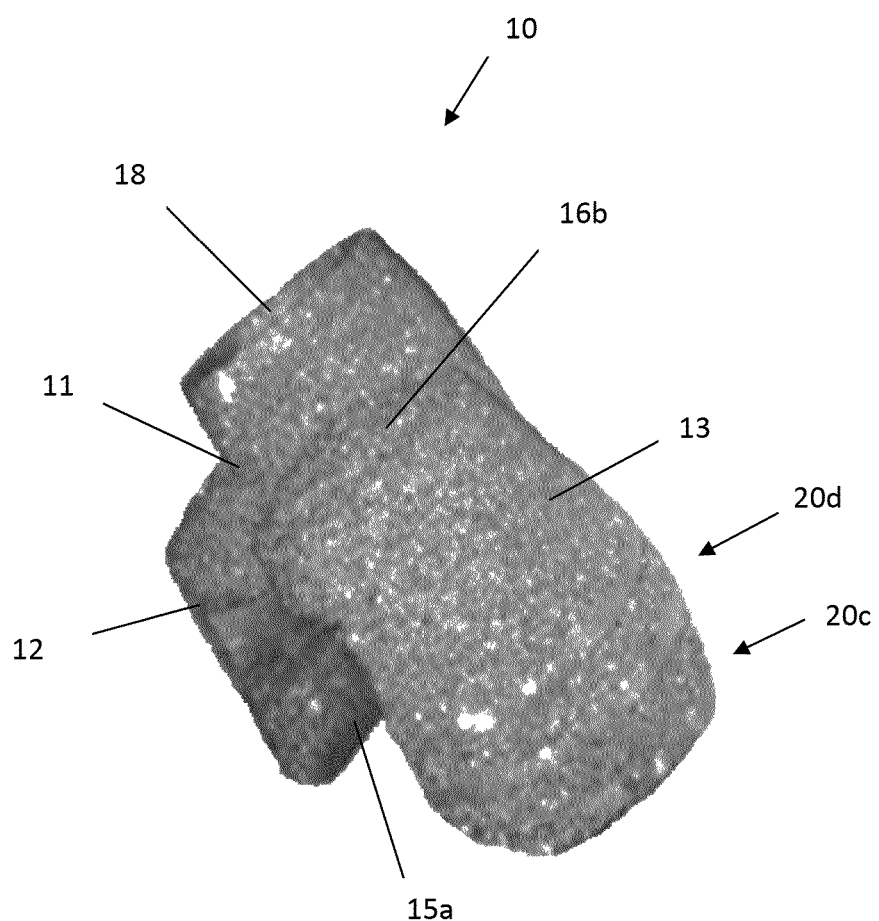
FIG. 4 shows a side perspective view of the void filling prosthesis of FIG. 1.

FIGS. 1-4 depict a first embodiment of a void filling prosthesis 10. The void filling prosthesis 10 includes a central body 11, a medial leg 13, and a lateral leg 12. In another embodiment, the void filling prosthesis 10 may include a central body and only a medial leg 13 or lateral leg 12. The central body 11 is generally cylindrical. However, this cylindrical shape may take the form of a portion that has a constant diameter and a portion that is slightly tapered such that it is generally frustoconical. The central body 11 includes an aperture 18 that extends through the central body 11 in order to allow the passage of an IM stem of a femoral component 30. This aperture 18 forms a wall 19, which is integrated with the lateral and medial legs 12, 13 forming a monolithic structure.

The lateral and medial legs 12, 13 may be offset posteriorly from a median transverse axis of the central body 11. Further, the lateral and medial legs 12, 13 may be located in close proximity, but may be separated generally by a space 17 that penetrates through both legs and forms a saddle-like structure in order to provide clearance for a femoral cam box 33 of a femoral component 30. This space 17 forms inner surfaces 15a-d that abut the femoral cam box 33 when implanted. These inner surfaces 15a-d may be flat, planar walls, or they may be terraced to provide surfaces conducive for bonding with bone cement. Further, inner surface 15d may be obliquely angled with respect to the longitudinal axis of the central body 11 in order to account for the angle of the IM stem (not shown) with respect to the cam box.

Further geometric features may be incorporated into the medial and lateral legs 12, 13 in order to provide clearance for the structure of the femoral component 30. For instance, inclined surfaces 14a-d may be fashioned into each leg in order to provide clearance for a bone interface surface 35 of the femoral component 30.

The remainder of the lateral and medial legs 12, 13 that has not been shaped to form clearance space is depicted as having a generally frustoconical profile. This geometric profile is preferred in order to conform more closely to bone voids created by the reaming instrumentation. However, this is merely an example of a geometry that the medial and lateral legs 12, 13 may form. The legs 12, 13 may have other geometries, such as box-like geometries. Further, the medial and lateral legs 12, 13 may be symmetric with respect to one another, or they may be asymmetric where one leg 12, 13 may be larger than the other 12, 13 and/or one leg 12, 13 may have a different geometry. A conical structure 16a-b may be disposed at one end of each of the lateral and medial legs 12, 13. This conical structure 16a-b may help prevent rotation of the prosthesis 10 when implanted in the bone and help the prosthesis 10 settle into the proper orientation and more closely conform to the void formed by the reaming instruments.

Referring to FIGS. 1-4 and 7-8, each leg 12, 13 is shown to include two removable portions 20a-d at an end of each leg 12, 13. While two removable portions 20a-d are shown, this is merely an example. Each leg 12, 13 may include any number of selectively removable portions 20a-d, including just one. Alternatively, one leg 12, 13 may include at least one selectively removable portion 20a-d while the other leg 12, 13 may have no selectively removable portions 20a-d. Where one or more selectively removable portions 20a-d is removed from a leg 12, 13, the length of the leg 12, 13 is decreased in order to make room in the joint cavity for a bone augment, for example. This removability provides the operator the operating room capability and flexibility to configure the void filling device 10 to work in conjunction with a bone augment, or alternatively work where no augment is needed. Thus, each selectively removable portion 20a-d is shaped to conform to the geometries of the void filling prosthesis 10 as though they will never be removed. Further, where these portions 20a-d are not removed, they provide structural support to the prosthesis 10.

Where there are multiple selectively removable portions 20a-d, they are layered along the length of each leg 12, 13 as far as needed to accommodate a bone augment. Each selectively removable portion 20a-d may have a first section 22a-d made from a weaker material and a second section 21a-f made from a stronger material, where the two sections 21a-f, 22a-d are layered along the length of each leg 12, 13. In a preferred embodiment, the weaker and stronger material may be made from the same metallic material, but the weaker material may have a higher porosity than that of the stronger material allowing for a seamless transition between these two sections 21a-f, 22a-d, but providing a region for easy separation. Separation is made easier by the fact that the more porous material is easier to separate and that the two sections 21a-f, 22a-d are visually recognizable indicating the separation location. In one embodiment, the separation location may be designated by a small chamfer to receive a cutting blade between the first section 22a-d of one selectively removable portion 20a-d and the second section 21a-f of another selectively removable portion 20a-d. An example of the porous metallic material may be titanium, titanium alloy, stainless steel, cobalt chrome alloys, tantalum or niobium formed by direct laser remelting as described in U.S. Pat. No. 7,537,664 titled "Laser-Produced Porous Surface," the entirety of which is incorporated-by-reference herein fully set forth herein and which is assigned to the same entity as the present invention. Additional examples are disclosed in U.S. application Ser. No. 11/027,421, filed Dec. 30, 2004, Ser. No. 11/295,008, filed Dec. 6, 2005, and Ser. No. 13/441,154, filed Apr. 6, 2012, and U.S. Pat. Nos. 8,350,186 and 8,147,861, the entireties of which are incorporated-by-reference herein as if fully set forth herein.

In an alternative embodiment, the weaker material may have the same porosity as the stronger material, but may be constructed from a material that has a lower modulus than the stronger material. In another embodiment, the entire void filling prosthesis 10 may be constructed from a porous metallic material including the selectively removable portions 20a-d with little or no variations in the porosity, but that the selectively removable portions 20a-d have score marks to designate the cutting points. In a further embodiment, the first section 22a-d may have an outer shell that is the same porosity as the remainder of the void filling prosthesis 10, and an interior portion constructed from the weaker material.

These selectively removable portions 20a-d may be removed by cutting along the weaker section 22a-d generally parallel and adjacent the stronger section 21a-f of another selectively removable portion 20b, 20d that is more proximate the central body using a cutting device. For instance a cutting device may be a guillotine-like device, an example of which is disclosed in U.S. application Ser. No. 12/002,002, filed Dec. 13, 2007, the entirety of which is incorporate-by-reference herein as if fully set forth herein. Where the selectively removable portion 20b, 20d is the last selectively removable portion along the length of that particular leg 12, 13, the leg 12, 13 may have a layer of stronger material 21c, 21f just adjacent to the weaker section 22b, 22d of that selectively removable portion 20b, 20d to facilitate removal.

The remainder of the void filling prosthesis 10 may also be partially constructed from porous metallic material as described above. In one embodiment, the surfaces in contact with the femoral component 30, such as internal surfaces 15a-d, may be constructed of solid metallic material, such as titanium as an example, while the remainder of the void filling prosthesis 10 may be constructed of porous metallic material.

Figure 5:
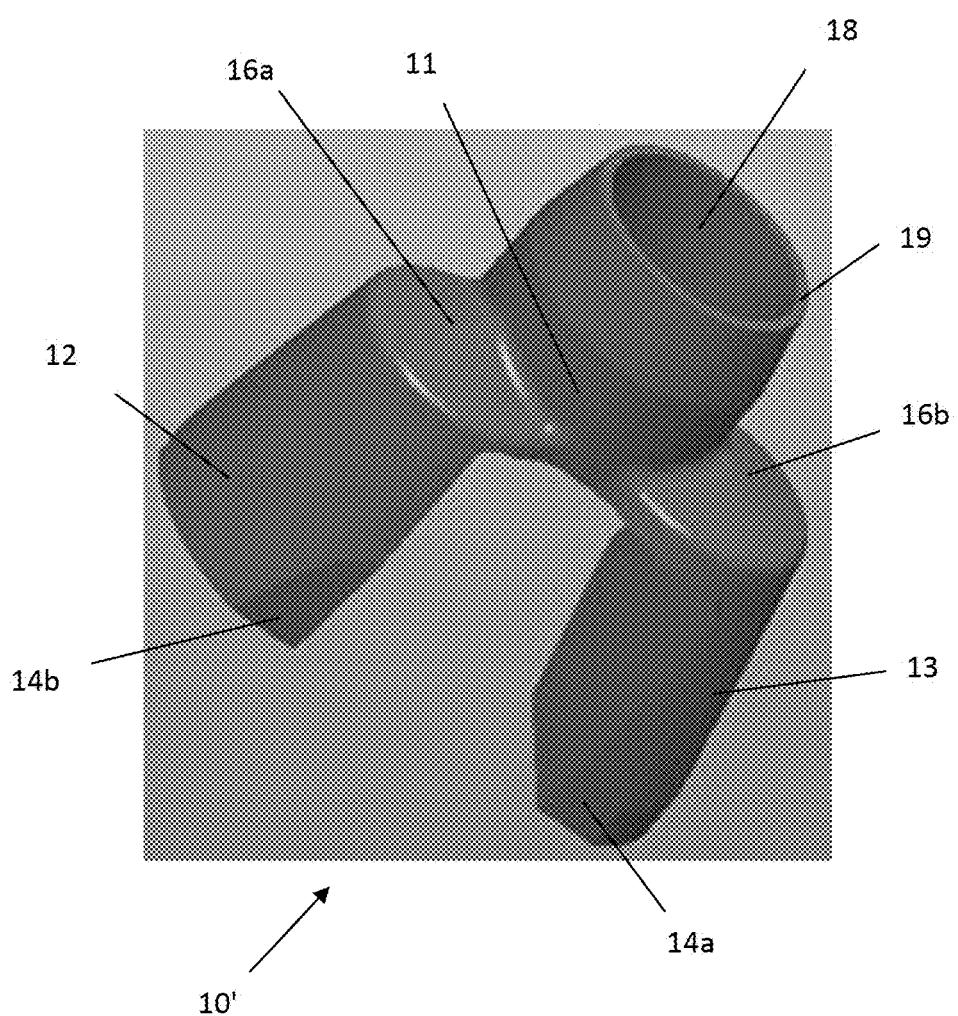
FIG. 5 shows a top perspective view of another embodiment of a void filling prosthesis of FIG. 1.
Figure 6:
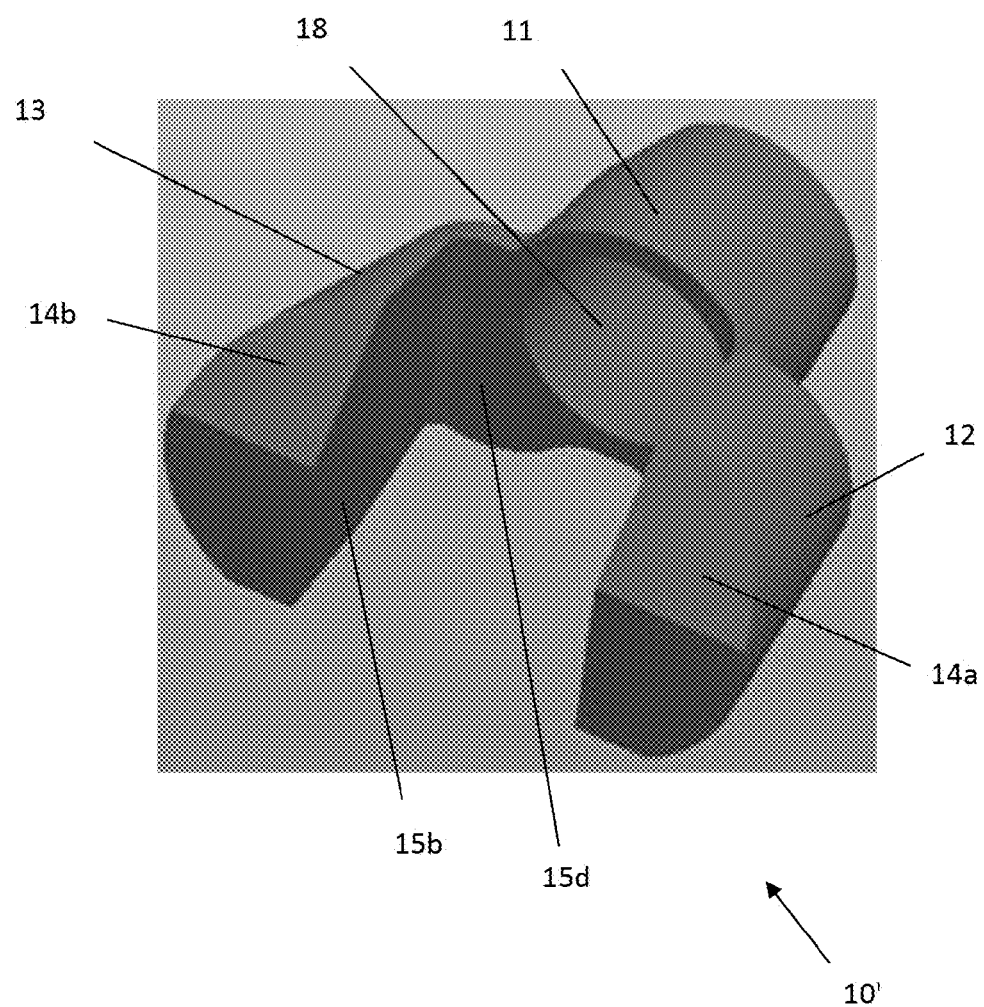
FIG. 6 shows a bottom perspective view of the void filling prosthesis of FIG. 5.
Figure 7:
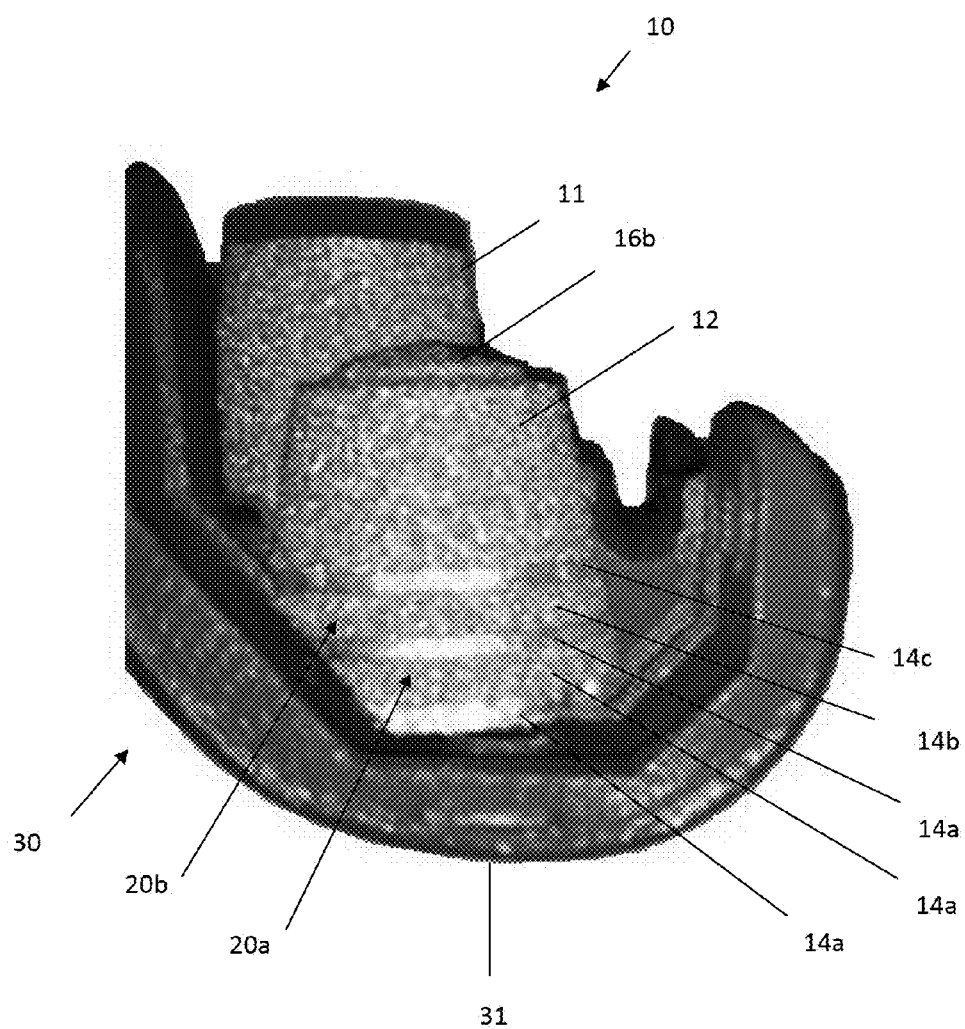
FIG. 7 shows a side view of the void filling prosthesis of FIG. 1 interfacing with a femoral component.
Figure 8:
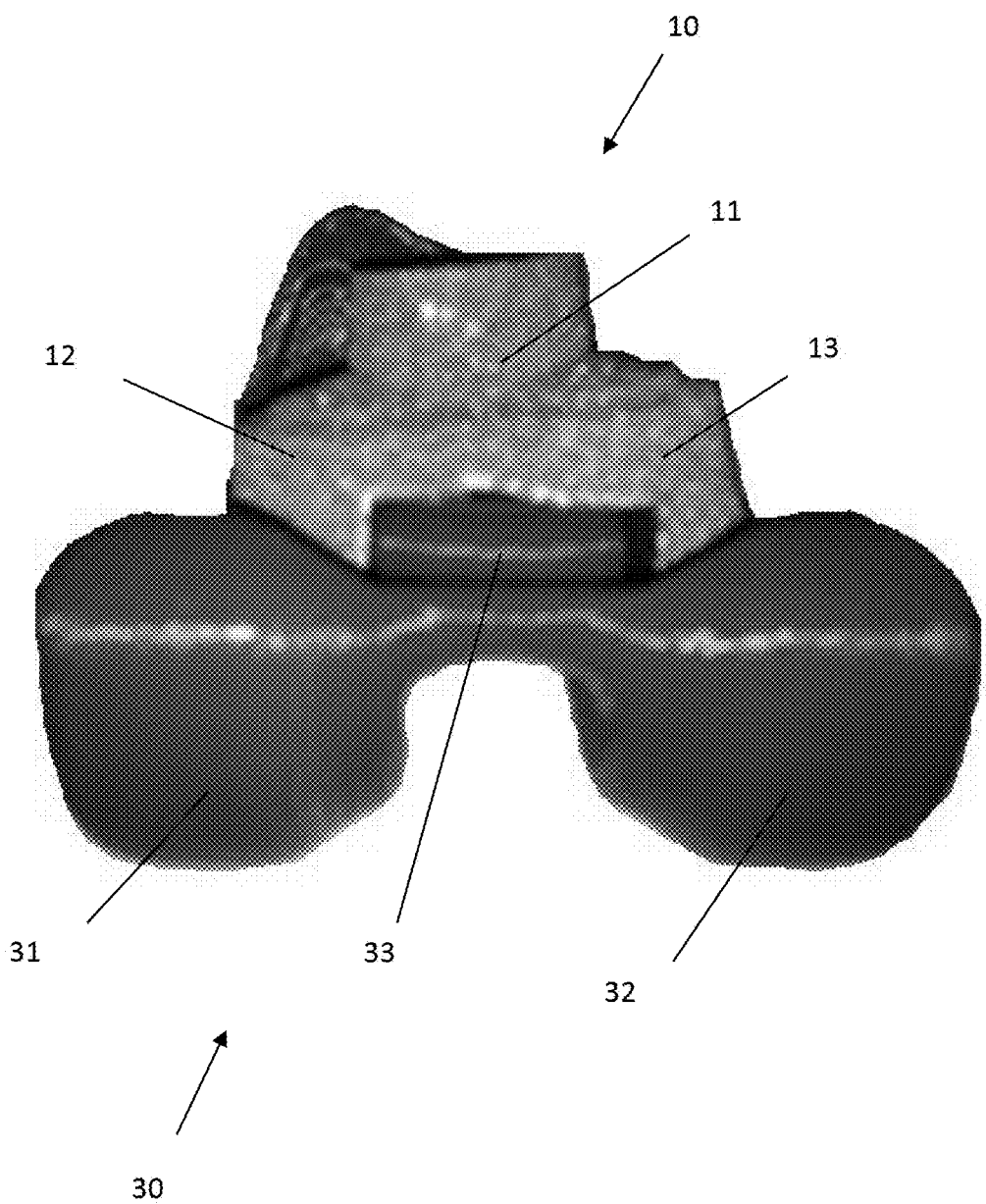
FIG. 8 shows a rear view of the void filling prosthesis of FIG. 1 interfacing with a femoral component.
Figure 9:
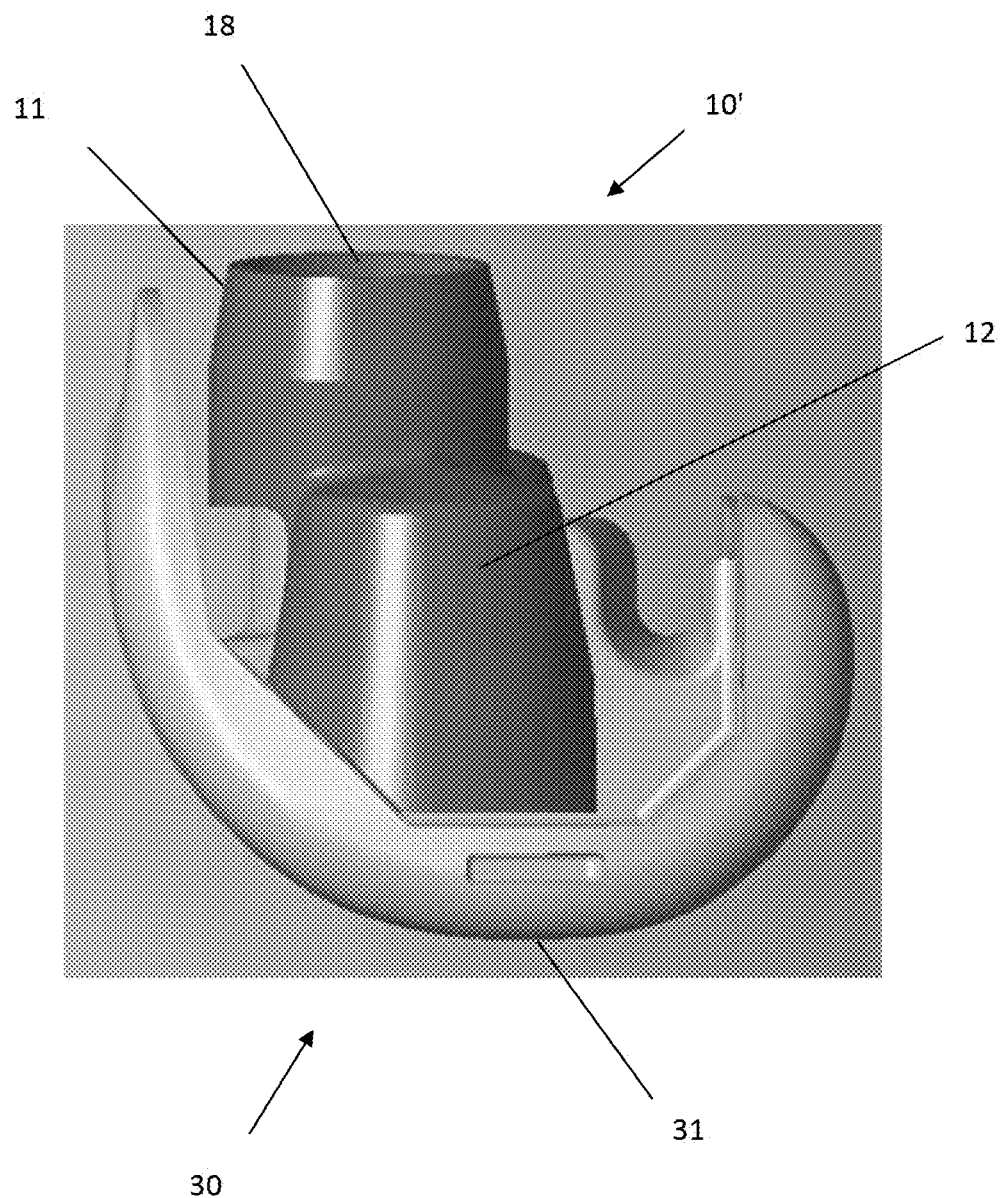
FIG. 9 shows a side view of the void filling prosthesis of FIG. 5 interfacing with a femoral component.
Figure 10:
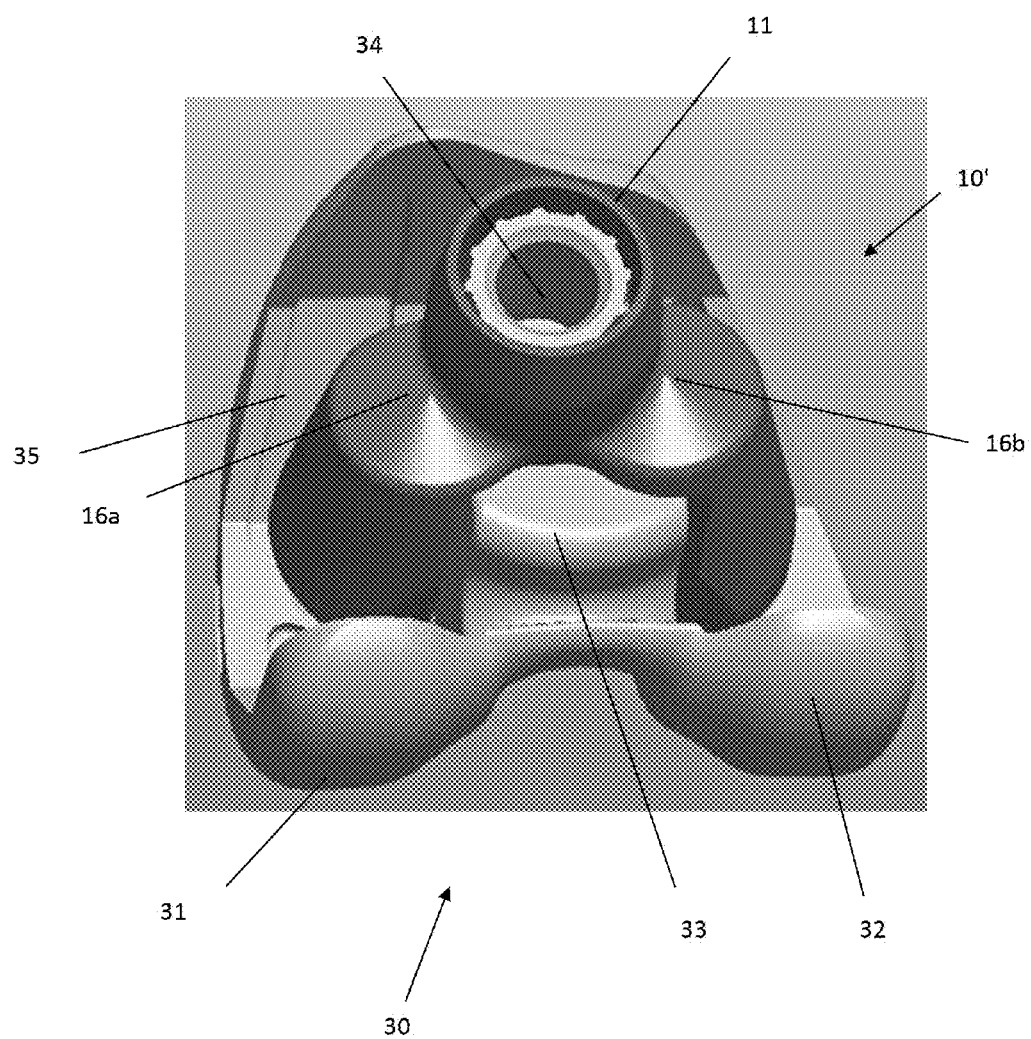
FIG. 10 shows a top perspective view of the void filling prosthesis of FIG. 5 interfacing with a femoral component.

FIGS. 5 and 6 depict an alternative embodiment wherein the bone void filler 10' does not include selectively removable portions 20a-d, but has substantially the same geometries as prosthesis 10. This embodiment may also be constructed from the same materials as that of prosthesis 10, including portions of porous metallic material. Further, this embodiment may also be constructed from solid metal or high strength polymeric material.

FIGS. 7-10 depict the interface between the void filling prosthesis 10, 10' and a femoral component 30. The femoral component 30 may be any femoral component 30, for example a femoral component 30 utilized in a posterior stabilized or total stabilized total knee prosthesis, for example the Scorpio® TS femoral component (Howmedica Osteonics, Mahwah, N.J.).

The void filling prosthesis 10, 10' may be placed in contact with the femoral component such that aperture 18 of the central body 11 is placed over a stem portion of the femoral component 30 and the inner surfaces 15a-d are placed in contact with the cam box 33. In one embodiment, bone cement is placed between the inner surfaces 15a-d and the cam box 33 to provide for additional support. Such inner surfaces 15a-d may be terraced to provide more surface area for bonding to the cement.

In one embodiment, the distal ends of the legs 12, do not contact the bone contacting surface 35 of the femoral component in order to provide some space for bone cement to flow and to provide space so that the operator can make minor corrections to the rotation of the femoral component 30.

A set of guided instruments may be provided to form the bone void to receive the void filling prosthesis. Included in this set of instruments may be an IM reamer 40, a boss reamer 50, a reamer guide assembly 60, an alignment handle 90, an alignment pin 100, a lobe reamer assembly 110, and a lobe trial 120.

Figure 11:
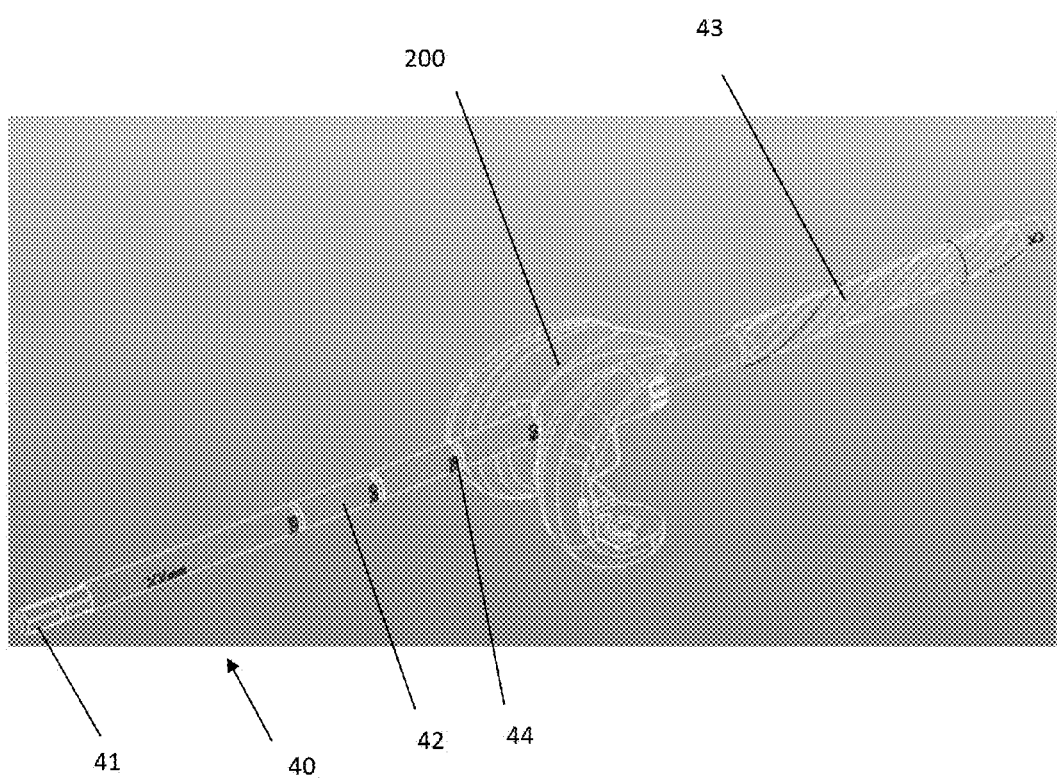
FIGS. 11-19 show a method and instrumentation for forming a bone void to receive the prostheses of FIG. 1 and FIG. 5.

The IM reamer 40, as depicted in FIG. 11, may include a shaft 42 that includes a plurality of depth indicators 44 situated along the length of the shaft 42 at designated intervals, and a reamer head 43 disposed at one end of the shaft. The other end of the shaft 41 may be configured to interface with a torque applying device, such as the chuck of a drill.

Figure 12:
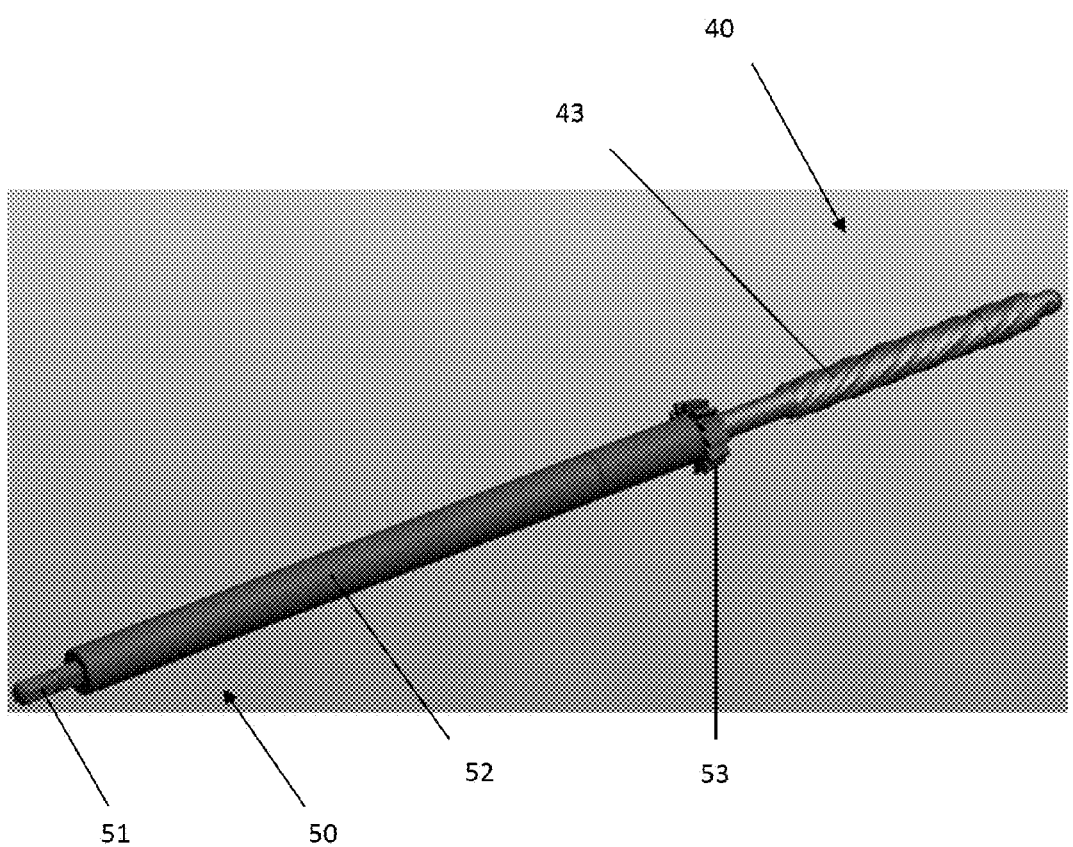

The boss reamer 50, as depicted in FIG. 12, may include a cannulated shaft 52 that includes a boss reamer head at one end. The other end 51 of the shaft 52 may be configured to interface with a torque applying device, such as the chuck of a drill. The internal diameter of the cannulated shaft 52 is such that the shaft 52 may be slid over the IM reamer shaft, but generally not the IM reamer head, and rotated with respect to the IM reamer. The boss reamer head may also be cannulated to slide over the IM reamer shaft 42 and may have a cutting diameter substantially similar to the diameter of the central body 11.

The reamer guide assembly 60, as depicted in FIGS. 13-19, may include a trial stem 70 and a reamer guide 80. The reamer guide generally includes a base 82, a support shaft 81, and a guide block 88. The trial stem 70 may be connected to one end of the base 82. In one embodiment, this connection may be a threaded connection, ball-detent connection or any other connection as is known in the art. The other end of the base 82 includes an abutment surface 89 and the support shaft 81 extending from the base 82 at an outward angle with respect the longitudinal axis of the trial stem 70. The support shaft 81 then bends such that the remainder of the support shaft 81 is generally parallel to the longitudinal axis of the trial stem 70. Integrated into the end of the guide shaft 81 is the guide block 88. The guide block 88 generally includes a handle hole 83 extending through the guide block 88 for receipt of an alignment handle 90 (described below), an alignment pinhole (not shown) for receipt of an alignment pin 100 (described below), and a first and second lobe reamer guide 84, 85. The first and second lobe reamer guides 84, 85 are generally disposed between the handle hole 83 and alignment pinhole. Both the first and second lobe reamer guides 84, 85 include a passageway 86a, 86b that is substantially cylindrical and a side-slot 87a, 87b extending through the sides of each of the lobe reamer guides 84, 85 into the passageway 86a, 896b. The longitudinal axes of the passageways 86a, 86b extend to a location on the abutment surface 89. Further, these longitudinal axes may be provided at various angles with respect to the longitudinal axis of the trial stem 70 in order to ream different bone void dimensions.

The alignment handle 90, as depicted in FIG. 14-19, is generally an elongate shaft with a flange disposed 91 along its length for abutting against the guide block 88. The alignment pin 100 is preferably a ⅛" diameter pin with a length long enough to extend beyond the epicondyles when inserted into the guide block 88. While ⅛" diameter is preferred so as to not obstruct the epicondyles from the operator's view, any diameter pin may be used.

The lobe reamer assembly 110, as depicted in FIGS. 15-17 and 19, includes a lobe reamer head 117, a reamer shaft 116, a depth stop collar 112, and a bushing 113. The lobe reamer head 117 is disposed at one end of the reamer shaft 116, while the other end 111 of the shaft 116 is configured to interface with a torque applying device. The depth stop collar 112 is fixed to the reamer shaft 116 opposite the end of the lobe reamer head 117. The reamer shaft 116 has a diameter small enough to fit through the side-slot 87a, 87b of the first and second reamer guides 84, 85. The bushing 113 is disposed along a portion of the reamer shaft 116 between the reamer head 117 and depth stop collar 114 such that the bushing 113 can slide back and forth between the reamer head 117 and depth stop collar 112. The bushing 113 is generally cylindrical and includes a first segment 115 and second segment 114 where the second segment 114 generally has a larger diameter than the first segment 115. The diameter of the first segment 115 may be dimensioned to slide into and fit tightly within the passageway 86a, 86b of the first and second lobe reamer guides 84, 85.

Figure 18:
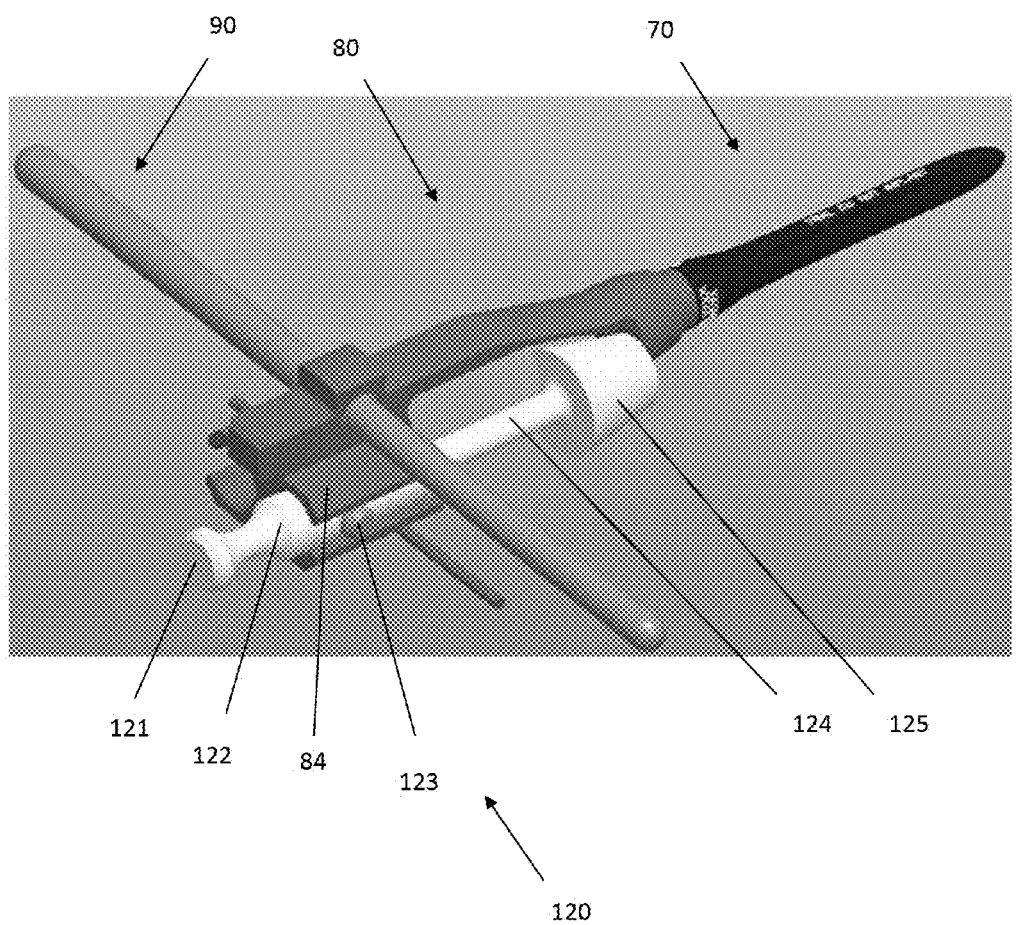
Figure 19:
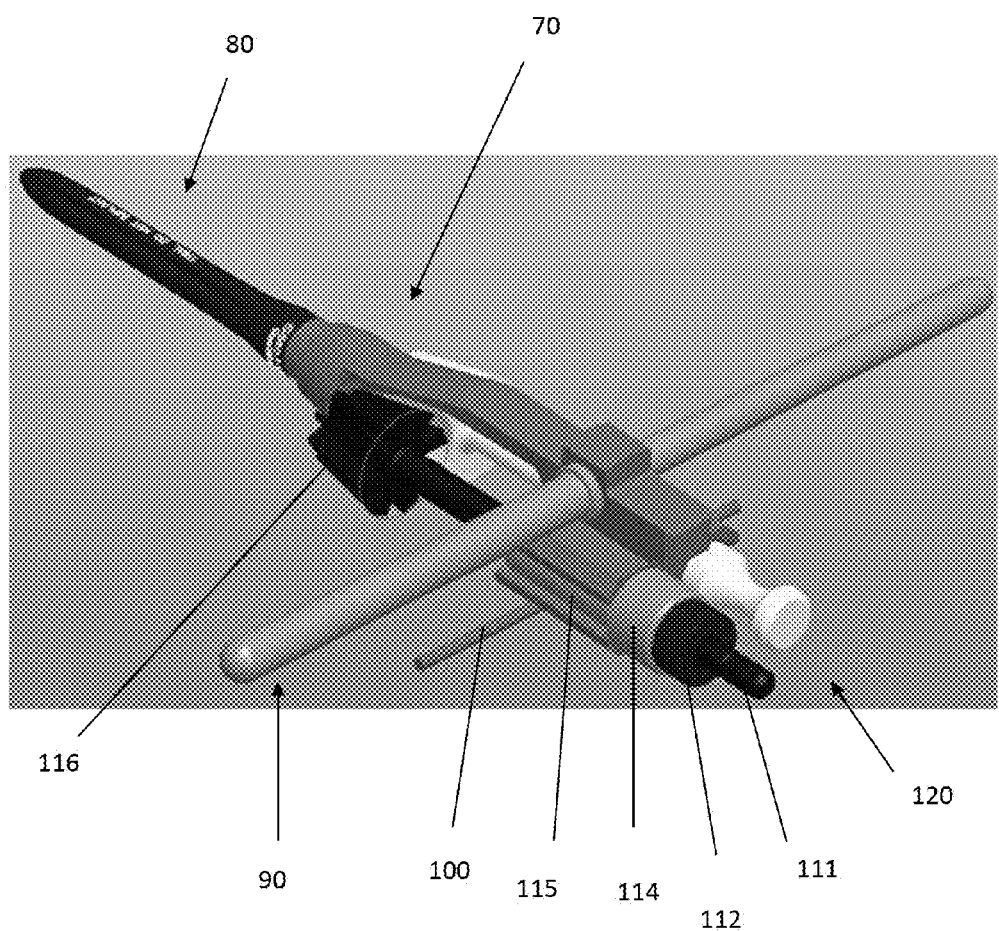

The lobe trial 120, as shown in FIGS. 18 and 19, includes a lobe trial head 125 and a first shaft segment 124 and a second shaft segment 122. The lobe trial head 125d is disposed at the end of the first shaft segment 124 and generally has a frustoconical shape with a portion removed along its length. The lobe trial head 125 is dimensioned to substantially match the bone void formed by the reamer head 116 and to substantially match at least one leg 12, 13 of the void filling prosthesis 10. While the lobe trial head 125 is depicted as having this shape, the lobe trial head 125 may have any shape depending on the shape of the reamer head 116 and the legs 12, 13 of the void filling prosthesis 10. The first shaft segment 124 has a diameter less than that of the second shaft segment 122 and is dimensioned to be capable of passing through the side-slot 87a, 87b of the first and second lobe reamer guides 84, 85. The second shaft segment 122 is dimensioned such that it can tightly fit and slide within the passageway 86a, 86b of the first and second lobe reamer guides 84, 85. An impact surface 121 is formed at the opposite end of the lobe trial 120 as that of the lobe reamer head 125. The impact surface 121 is a relatively broad and flattened surface so that the operator can impact the lobe trial 70 in order to seat the lobe trial head 125 into a bone void.

In one embodiment of the present invention, a method for forming a void in bone to receive the void filling prosthesis 10, as illustrated by FIGS. 11-19. In this embodiment, the instruments, as described above, are utilized. While FIGS. 11-19 and the following description of the method are directed toward the preparation of a bone void within a femur, it is to be understood that this is merely an example. The following method may be utilized to prepare a bone void in any long bone.

Referring to FIG. 11, the IM reamer 40 is depicted as reaming along the IM canal of a femur 200 until the bone 200 is flush with the requisite depth indicator 44. While it appears from FIG. 11 that the IM reamer 40 is passing through a femoral component, the femoral component is merely a depiction of the femur 200. With the IM reamer 40 remaining within the IM canal, the boss reamer 50 is slid over the shaft of the IM reamer, as shown in FIG. 12. The operator reams along the IM reamer shaft 42 until the boss reamer head 53 abuts the IM reamer head 40, thereby preventing further travel into the femur bone 200. The IM reamer and boss reamer 50 are then removed from the IM canal in preparation for further bone forming.

Figure 13:
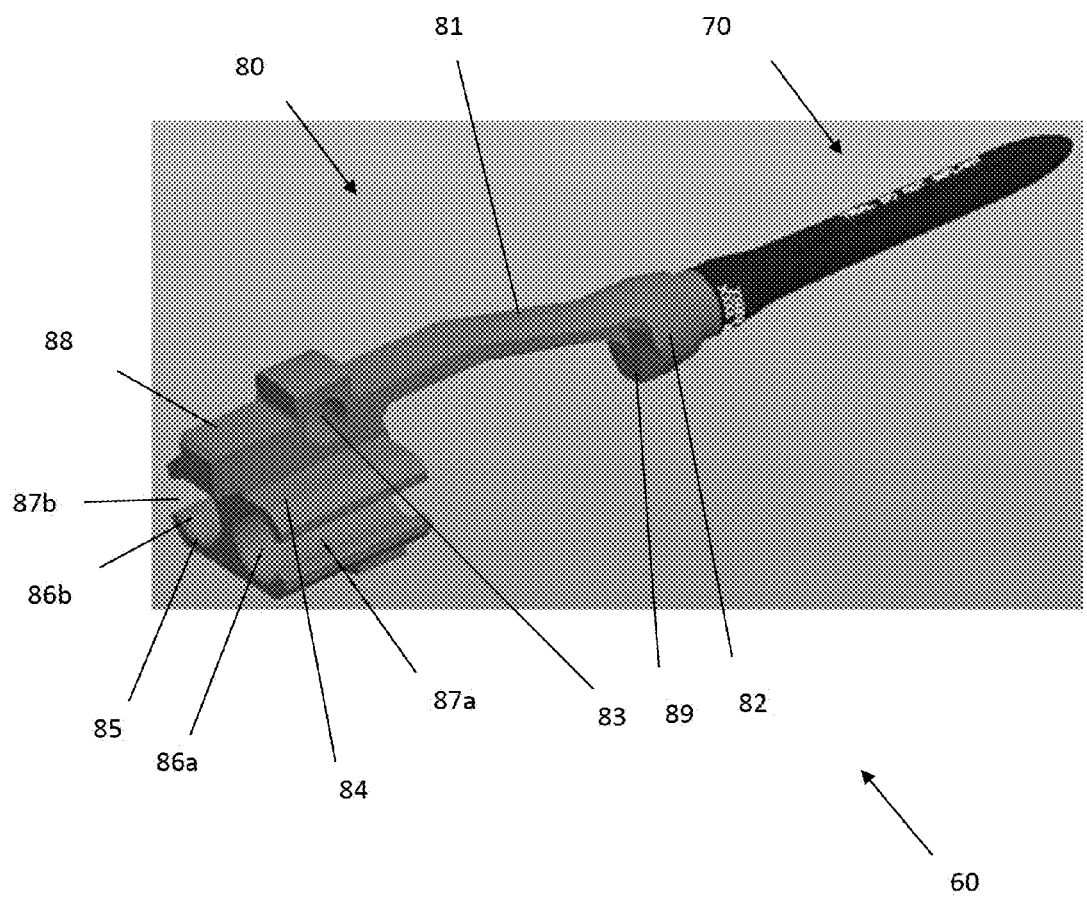

Referring to FIG. 13, the reamer guide assembly 60 is assembled. In such assembly, the operator may select a trial stem 70 to match the IM reamer head diameter, and then attach the trial stem 70 to the reamer guide 80. In another embodiment, the IM reamer 40 may be attached to the reamer guide 80, thus taking the place of the trial stem 70. Attachment may be by a threaded engagement, with a ball detent, or any other engagement known in the art. Once the reamer guide assembly 60 is assembled, the trial stem 70 is inserted into the portion of the IM canal that was reamed by the IM reamer 40, and the base of the reamer guide 82 is inserted into the portion of bone reamed by the boss reamer 50. The operator may further seat the reamer guide assembly 60 to the proper depth by impacting the end of the guide block 88. The proper depth may be indicated when the reamer guide assembly 110 no longer moves when impacted and generally where the bone is flush with the bend in the support shaft 81.

Figure 14:
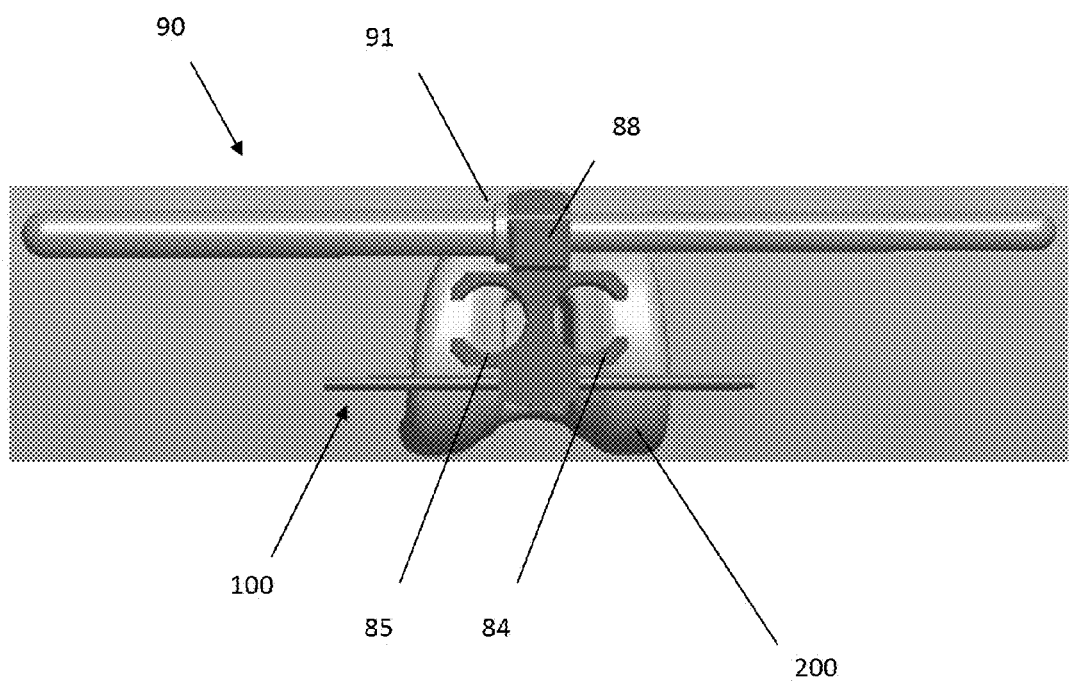

Referring to FIG. 14, with the reamer guide assembly 60 firmly seated within the IM canal, the alignment handle 90 is placed in the handle hole 83 until the flange 91 abuts the guide block 88, and the alignment pin 100 is placed in the alignment pinhole such that the alignment pin 100 extends from both sides of the guide block 88 beyond the periphery of the femur. The operator will then grip the alignment handle 90 and rotate the reamer guide assembly 60 within the IM canal until the alignment pin 100 is aligned with the transepicondylar axis or any axis of the operator's preference.

Figure 15:
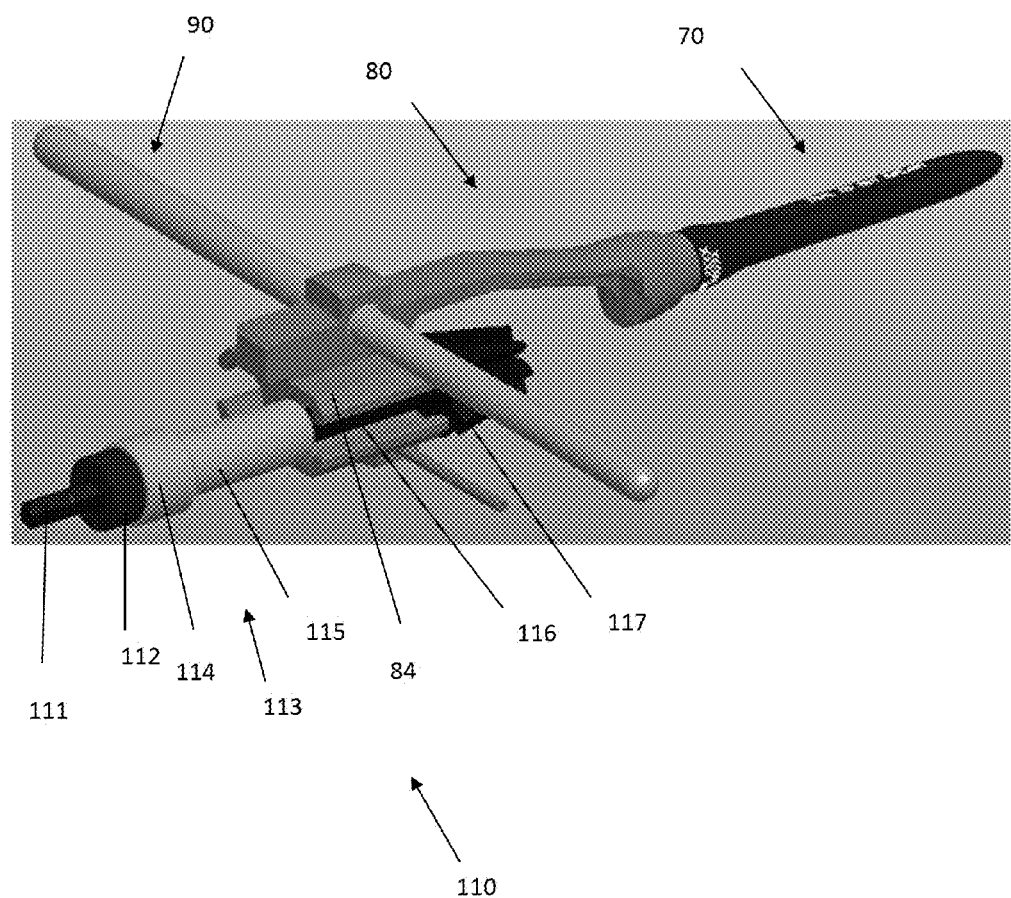
Figure 16:
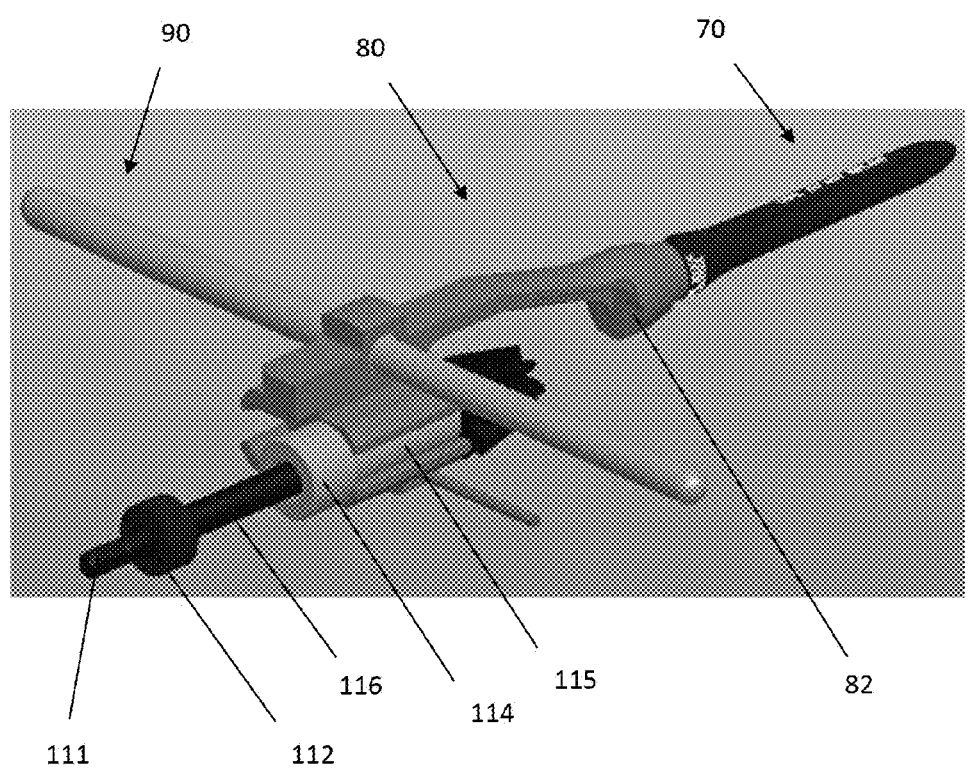
Figure 17:
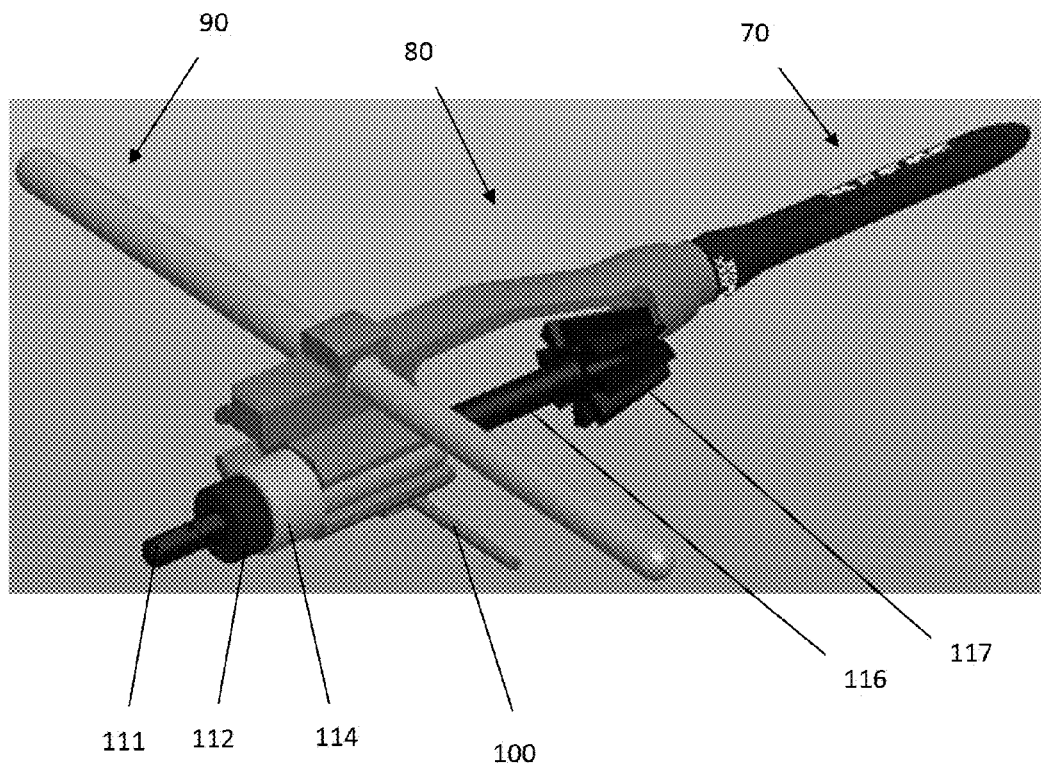

Referring to FIG. 15, once alignment is achieved the lobe reamer assembly 110 is loaded into the first lobe reamer guide 84. This is achieved by moving the bushing 113 so that it abuts the depth stop collar 112, thereby exposing the reamer shaft 116 proximate to the reamer head 117. The reamer shaft 116 is then side-loaded through the side-slot 87a and into the passageway 86a. The resulting configuration should be such that the reamer head 116 is located on one side of the first lobe reamer guide 84 and the bushing 113 located on the other side, as shown in FIG. 15. The first segment 115 of the bushing 113 is then slid into the passageway 86a until the second segment 113 abuts the first lobe reamer guide 84, as shown in FIG. 16. The reamer head 116 is then advanced into the distal femur by applying a torque to the reamer shaft 115 until the depth stop collar 112 abuts the bushing 113 and the reamer head 116 abuts the abutment surface 82, as shown in FIG. 17. The reamer head 116 is then retracted from the femur and the reamer assembly 110 removed from the first lobe reamer guide 84 through the side-slot 87a.

Referring to FIG. 18, the lobe trial 120 is then loaded into the passageway 86a of the first lobe reamer guide 84 in a similar fashion as the lobe reamer assembly 110. The first shaft segment 124 of the lobe trial 120 is passed through the side-slot 87a and into the passageway 86a. The lobe trial head 125 is then advanced into the first bone void. As the lobe trial head 125 is advanced, the second shaft segment 123 is advanced into the passageway 86a and the lateral protrusion 123 is advanced into the side-slot 87a. The lateral protrusion 123 ensures that the lobe trial 120 has the proper rotational alignment and also acts as a stop to prohibit rotation. In one embodiment of the lobe trial 120, the lateral protrusion 123 may be a pin that extends through the second shaft segment 122 and into a hole located in the first lobe reamer guide 84 to prevent both rotational and translational movement. The operator may then impact the impact surface 121 to fully seat the lobe trial 120. The lobe trial 120 may remain in place while a second bone void is formed in order to provide additional stability during reaming, as seen in FIG. 19.

Referring to FIG. 19, the lobe reamer assembly 110 is side-loaded into the second lobe reamer guide 85 as previously described. The reamer head 117 is then advanced into the distal femur by applying a torque to the reamer shaft 116 until the depth stop collar 112 abuts the bushing 113 and the reamer head 117 abuts the abutment surface 89, thereby forming a second bone void for receipt of the void filling prosthesis 10.

While this method has generally been described herein as utilizing one lobe reamer assembly 120 to form both bone voids, more than one lobe reamer assembly 110 having different geometries may be used depending on the geometry of the void filling prosthesis 10.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for reaming bone, comprising:
    an intramedullary member having first and second ends and a longitudinal axis extending in a first direction between the first and second ends; and
    a guide member coupled to the first end of the intramedullary member and having a body, a base, and a support shaft, the base being coupled to the intramedullary member, the support shaft being coupled to the body and the base, the body having first and second apertures each extending entirely through at least a portion of the body, the first aperture having a first length defining a first axis, the second aperture having a second length defining a second axis, the first and second apertures being oriented with respect to the intramedullary member such that the first and second axes each extend in the first direction and are offset from the longitudinal axis of the intramedullary member.

2. The system of claim 1, wherein the intramedullary member is an intramedullary rod slidingly coupled to the guide member.

3. The system of claim 1, wherein the intramedullary member is a trial stem fixedly coupled to the guide member.

4. The system of claim 1, wherein the first and second axes are parallel with the longitudinal axis of the intramedullary member.

5. The system of claim 1, further comprising:
    a first slot extending through a first sidewall defined by the first aperture and along the length of the first aperture, and
    a second slot extending through a second sidewall defined by the second aperture and along the length of the second aperture.

6. The system of claim 5, further comprising a reamer having a cutting head and a shaft extending from the cutting head, the shaft extending through the first aperture.

7. The system of claim 6, wherein the shaft has a cross-sectional dimension smaller than a width defined by the first and second slots.

8. The system of claim 6, wherein the reamer further includes a flange extending radially outwardly from the shaft and a bushing slidingly coupled to the shaft between the flange and the cutting head.

9. The system of claim 6, wherein the bushing has a first portion and a second portion, the first portion receivable within the first aperture, the second portion not receivable within the first aperture.

10. The system of claim 6, wherein the cutting head has a frustoconical geometry.

11. The system of claim 1, wherein the base includes an abutment surface positionally located to partially inhibit movement of a reamer extending through one of the first aperture or second aperture.

12. A system for reaming bone, comprising:
an intramedullary member having a first end and a longitudinal axis extending in a first direction;
a guide member coupled to the first end of the intramedullary member and having a body, the body having a first aperture and a first slot, the first aperture having a length extending entirely through at least a portion of the body, the first slot extending through a first sidewall defined by the first aperture and along the length of the first aperture; and
a reamer having a cutting head and a shaft extending from the cutting head, the shaft being sized to pass through the first slot and into the first aperture.

13. The system of claim 12, wherein the body further includes a second aperture and a second slot, the second aperture having a length extending entirely through the at least a portion of the body, the second slot extending through a second sidewall defined by the second aperture and through the second sidewall along the length of the second aperture.

14. The system of claim 12, wherein the shaft has a cross-sectional dimension smaller than a width defined by the first slot.

15. The system of claim 14, wherein the reamer further includes a flange extending radially outwardly from the shaft and a bushing slidingly coupled to the shaft between the flange and the cutting head.

16. The system of claim 15, wherein the bushing has a first portion and a second portion, the first portion receivable within the first aperture, the second portion not receivable within the aperture.

17. The system of claim 12, further comprising a trial having a trial head, a first shaft segment, and a second shaft segment, the trial head having a frustoconical profile, the first shaft segment have a diameter smaller than a width defined by the first slot, the second shaft segment having a diameter larger than the width defined by the first slot.

18. A method of forming a bone void in bone for receipt of a prosthesis, comprising:
inserting an intramedullary member at least partially into an intramedullary canal of the bone;
guiding a reamer through a first aperture of a guide member while the intramedullary member is at least partially inserted into the intramedullary canal, the guide member being coupled to an end of the intramedullary member;
reaming a first offset bone void with the reamer while the reamer is at least partially disposed within the first aperture, the first offset bone void at least partially overlapping with a central bone void;
guiding the reamer through a second aperture of the guide member; and
reaming a second offset bone void with the reamer while the reamer is at least partially disposed within the second aperture, the second offset bone void at least partially overlapping with the central bone void.

19. The method of claim 18, wherein the bone is a femur bone.

20. The method of claim 18, further comprising:
reaming the central bone void coaxially with the intramedullary canal.

21. The method of claim 19, further comprising:
assessing the rotational alignment of the guide member with respect to the femur bone with an alignment pin extending through the guide member in a transverse direction.

22. The method of claim 21, wherein the assessing step incudes viewing the alignment pin with respect to an epicondylar axis of the femur bone.

23. The method of claim 18, further comprising:
loading the reamer into the first aperture through a first slot extending through a first sidewall of the guide member.

24. The method of claim 21, further comprising:
removing the reamer from the first aperture through the first slot; and
loading the reamer into the second aperture through a second slot extending through a second sidewall of the guide member.

* * * * *